(12) United States Patent
Suhadolnik

(10) Patent No.: US 6,207,366 B1
(45) Date of Patent: Mar. 27, 2001

(54) CHRONIC FATIGUE SYNDROME DIAGNOSIS

(75) Inventor: Robert J. Suhadolnik, Roslyn, PA (US)

(73) Assignee: Temple University- Of the Commonwealth System of Higher Education, Phila., PA (US)

( * ) Notice: Subject to any disclaimer, the term of this patent is extended or adjusted under 35 U.S.C. 154(b) by 0 days.

(21) Appl. No.: 09/548,582

(22) Filed: Apr. 13, 2000

Related U.S. Application Data

(60) Provisional application No. 60/129,265, filed on Apr. 14, 1999.

(51) Int. Cl.$^7$ ............................... C12Q 1/00; C12Q 1/34; G01N 33/53; G01N 33/573
(52) U.S. Cl. ............................... 435/4; 435/7.1; 435/7.4; 435/7.72; 435/18
(58) Field of Search ..................... 435/47.1, 7.4, 435/7.72, 18

(56) References Cited

U.S. PATENT DOCUMENTS

| | | | |
|---|---|---|---|
| 4,990,498 | 2/1991 | Suhadolnik | 514/47 |
| 5,258,369 | 11/1993 | Carter | 514/44 |
| 5,776,690 | 7/1998 | Vojdani et al. | 435/6 |
| 5,985,565 | 11/1999 | Suhadolnik | 435/6 |

FOREIGN PATENT DOCUMENTS

| | | |
|---|---|---|
| 0 285 263 B1 | 3/1988 | (EP). |
| 0 325 018 A2 | 3/1988 | (EP). |
| 0 525 917 A2 | 7/1988 | (EP). |
| 0 306 347 A2 | 9/1988 | (EP). |
| WO 91/00097 | 1/1991 | (WO). |

OTHER PUBLICATIONS

Suhadolnik et al., "Further Evidence for Biochemical Defects in the 2–5A Synthetase/RNase L and PKR Pathways in Chronic Fatigue Syndrome", *First World Congress On Chronic Fatigue Syndrome And Related Disorders*, Brussels, Nov. 9–11, 1995.

Suhadolnik et al., "Biochemical Dysregulation of the 2–5A/RNase L Antiviral Defense Pathway in Chronic Fatigue Syndrome",*Fourth International AACFS Research & Clinical Conference on CFIDS, Cambridge, Massachusetts*, Oct. 10–12, 1998.

De Meirleir et al., "Rnase L Dysfunction Disorder (R.E.D.D.) in CFS", *Fourth International AACFS Research & Clinical Conference on CFIDS, Cambridge, Massachusetts*, Oct. 10–12, 1998.

Horvath et al., "Characterization of RNase L Dysfunction in Peripheral Blood Mononuclear Cell Extracts from Patients with Chronic Fatigue Syndrome", *Fourth International AACFS Research & Clinical Conference on CFIDS, Cambridge, Massachusetts*, Oct. 10–12, 1998.

Bisbal et al., "A 2–5A Polypeptide of 37kDa as a Potential Biochemical Marker For Chronic Fatigue Syndrome", Abstract P5–2, p. S47 *J. Interferon & Cytokine Research*, 17(Suppl 2) (Oct. 1997).

Ning Kon and Robert J. Suhadolnik, "Indentification of the ATP Binding Domain of Recombinant Human 40–kDa 2',5'–Oligoadenylate Synthetase by Photoaffinity Labeling with 8–Azido–[$\alpha$–$^{32}$P]ATP*", *The Journal of Biological Chemistry*, 271(33):19983–19990 (Aug. 16, 1996).

Charubaia et al., "Chemical Synthesis of Adenylyl–(2'–5')–adenylyl–(2'–5')–8–azidonadenosine, and Activation and Photoaffinity Labelling of Rnase L by $^{32}$Plp5'A2'p5'A2'p5'N$_3$$^8$A", *Helvetica Chimica Acta*, 72:1354–1361 (1989).

Suhadolnik et al., "Upregulation of the 2–5A Synthetase/ RNase L Antiviral Pathway Associated with Chronic Fatigue Syndrome", *Clinical Infectious Diseases*, 18(Suppl 1):S96–104 (1994).

Suhadolnik et al., "2–and 8–Azido Photoaffinity Probes. 1. Enzymatic Synthesis, Characterization, and Biological Properties of 2–and 8–Azido Photoprobes of 2–5A and Photolabeling of 2–5A Binding Proteins", *Biochemistry*, 27:8840–8846 (1988).

Suhadolnik et al., "Changes in the 2–5A Synthetase/RNase L Antiviral Pathway in a Controlled Clinical Trial with Poly(I)–Poly(C$_{12}$U) in Chronic Fatigue Syndrome", In vivo, 8:599–604 (1994).

Salehzada et al., "Regeneration of Enzyme Activity After Western Blot: Activation of Rnase L by 2–5A on Filter— Importance for Its Detection", *Analytical Biochemistry*, 196:410–414 (1991).

Suhadolnik et al., "Biochemical Evidence for a Novel Low Molecular Weight 2–5A–Dependent Rnase L in Chronic Fatigue Syndrome", *Journal of Interferon & Cytokine Research*, 17:377–385 (Jul. 1997).

*Primary Examiner*—Robert A. Schwartzman
*Assistant Examiner*—Katharine F Davis
(74) *Attorney, Agent, or Firm*—Seidel, Gonda, Lavorgna & Monaco, PC

(57) ABSTRACT

Chronic fatigue syndrome is diagnosed through quantification of low and high molecular weight forms of RNase L in cellular extracts of RNase L-containing cells such as peripheral blood mononuclear cells. A ratio of low to high molecular weight RNase L of more than 0.15 is characteristic of chronic fatigue syndrome.

15 Claims, No Drawings

US 6,207,366 B1

CHRONIC FATIGUE SYNDROME DIAGNOSIS

CROSS-REFERENCE TO RELATED APPLICATION

The benefit of the filing date of U.S. provisional patent application Ser. No. 60/129,265, filed Apr. 14, 1999, is hereby claimed.

REFERENCE TO GOVERNMENT GRANT

The invention described herein was made in the course of work supported by U.S. Public Health Service grant RO1 Al38378. The United States government has certain rights in the invention.

FIELD OF THE INVENTION

This invention relates to the diagnosis of chronic fatigue syndrome (CFS) through detection and quantitation of RNase L molecules.

BACKGROUND OF THE INVENTION

CFS is an illness of unknown etiology, often associated with sudden onset, flu-like symptoms, debilitating fatigue, low-grade fever, myalgia and neurocognitive dysfunction. CFS patients typically display reduced Karnofsky performance scores (KPS). The Karnofsky performance test measures an individual's ability to function and carry on normal activities. Karnofsky scores range form zero for a dead patient to 100 for no evidence of disease. Diagnosis of CFS remains one of exclusion.

An accumulating body of evidence suggests that CFS is associated with disregulation of both humoral and cellular immunity, including mitogen response, reactivation of viruses, abnormal cytokine production, diminished natural killer cell function and changes in intermediary metabolites. It has been suggested that the clinical and immunological abnormalities observed in CFS might include defects in the double-stranded RNA (dsRNA)dependent, interferon-inducible pathways, i.e., the 2',5'-oligoadenylate (2-5A) synthetase/RNase L and p68 kinase (PKR) antiviral defense pathways (Suhadolnik et al., *Clin. Infect. Dis.* 18:S96–S104, 1994; Suhadolnik et al., *In Vivo* 8:599–604(1994). The 2-5A synthetase/RNase L pathway is part of the antiviral defense mechanism in mammalian cells; this pathway also has a role in the regulation of cell growth and differentiation (Lengyel, *Ann. Review Biochem.* 51:251–282, 1982; Sen et al., *Adv. Virus Res.* 42:57–102, 1993).

When activated by dsRNA, 2-5A synthetase converts ATP to 2',5'-linked oligoadenylateswith 5'-terminal phosphates. Biologically active 2-5A binds to and activates a latent endoribonuclease, RNase L, which hydrolyzes single-stranded viral and cellular RNA, primarily after UpNp sequences, thereby inhibiting protein synthesis.

Previous studies on the 2-5A synthetase/RNase L pathway in CFS revealed a statistically significant dysregulation in which the 2-5A synthetase is present predominantly in its activated form, bioactive 2-5A levels are elevated, and RNase L activity is upregulated (Suhadolnik et al., *Clin. Infect. Dis.*, supra; Suhadolnik et al., *In Vivo*, supra). Expression of the serine-threonine kinase, PKR, is downregulated in CFS (Suhadolnik et al., *In Vivo*, supra). PKR controls initiation of protein translation through phosphorylation of eIF-2.

Despite these efforts, a clear cut molecular marker for CFS has not been identified. Diagnosis is presently carried out with resort to criteria recommended by the Centers for Disease Control and Prevention (Fukuda et al., *Ann. Intem. Med.* 121:953–959, 1994). What is needed is a biochemical test, relying on an unambiguous molecular markers for CFS, which may form the basis of a definitive CFS diagnosis, or which may be employed as an adjunct to other CFS diagnostic methods.

Abbreviations

The following abbreviations may be used herein:

AMP: adenosine 5'-monophosphate;
2-Azido-AMP: 2-azidoadenosine 5'-monophosphate;
8-Azido-AMP: 8-azidoadenosine 5'-monophosphate;
2,8-Azido-AMP: 2,8-diazidoadenosine 5'-monophosphate;
2-5A: 2',5'-oligoadenylate, that is, an oligomer of adenylic acid with (2'→5')-phosphodiester linkages and 5'-riphosphate;
CFS: chronic fatigue syndrome;
dsRNA: double-stranded RNA;
ELISA: enzyme-linked immunosorbent assay;
etheno-AMP $N^1N^6$-ethenoadenosine 5'-monophosphate;
GST: glutathione S-transferase;
HEPES: 4-(2-hydroxyethyl)-piperazine ethanesulfonic acid;
PBMC: peripheral blood mononuclear cells;
PBS: phosphate-buffered saline;
$p_3A_3$ trimer of adenylic acid with (2'→5')-phosphodiester linkages and 5'-triphosphate;
pApAp(8-azidoA): 5'-O-phosphoryl-adenylyl-(2'→5')-adenylyl-(2'→5')-8-azidoadenosine;
poly(U)-3'-pCp: polyuridylic acid having a cytosine residue attached to the 3'terminus thereof;
SDS-PAGE: sodium dodecylsulfate-polyacrylamide gel electrophoresis.

SUMMARY OF THE INVENTION

A method for diagnosing chronicfatigue syndrome comprises determining the level of low molecular weight RNase L and the level of high molecular weight RNase L in a biological sample from a human subject; and computing a ratio for the level of low molecular weight RNase L to the level of high molecular weight RNase L, which ratio is diagnostic for chronic fatigue syndrome.

According to an embodiment of the invention, a ratio of low molecular weight RNase L to high molecular weight RNase L of greater than 0.15 indicates that the individual is afflicted with chronic fatigue syndrome.

The biological sample preferably comprises blood or a fraction thereof, most preferably a cytoplasmic extract of peripheral blood mononuclear cells.

According to one embodiment of the invention, the level of the low and high molecular weight RNase L are determined by (a) contacting the sample with a probe comprising a compound according to formula I bearing a detectable label, under conditions sufficient to form covalent conjugates of the labeled probe compound and 2',5'-oligoadenylate-binding proteins in the sample:

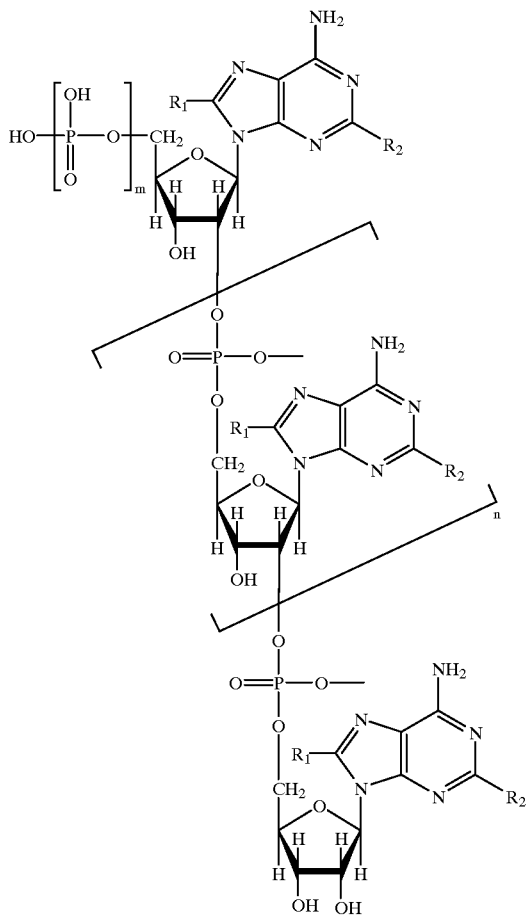

wherein
 m is an integer from 0 to 3,
 n is an integer from 1 to 3, and
 each $R_1$ and each $R_2$ is, independently of each other $R_1$ and $R_2$, hydrogen or $N_3$, provided at least one $R_1$ or $R_2$ is $N_3$, or a water soluble salt of said compound;

(b) contacting the sample containing the covalent conjugates with an antibody which binds RNase L species in the sample;

(c) separating the proteins in the sample by gel electrophoresis; and (d) quantitating the proteins of about 37 kDa and about 80 kDa apparent molecular weight according to sodium dodecyl sulfate-polyacrylamide gel electrophoresis, which about 37 kDa and about 80 kDa proteins have formed covalent conjugates with the labeled probe compound and which are bound by the antibody.

By "about" with reference to the molecular weight of the various RNase L forms is meant a molecular weight with the range of plus or minus 3 kDa.

DETAILED DESCRIPTION OF THE INVENTION

Biologically active 2-5A binds to and activates the latent endoribonuclease, RNase L. Activated RNase L in turn hydrolyzes single-stranded viral and cellular RNA, thereby inhibiting protein synthesis. Cell extracts from healthy individuals contain an about 80 kDa 2-5A binding protein (hereinafter "high molecular weight RNase L") with 2-5A-dependent RNase L activity. CFS patients, on the other hand, have been demonstrated to possess a distinct about 30 kDa 2-5A binding protein having 2-5A-dependent RNase L activity (hereinafter "low molecular weight R Nase L"). By "RNase L activity" is meant the enzymatic activity of RNase L in hydrolyzing its RNA substrates. The 30 kDa RNase L identifiable in cell extracts from individuals with CFS has the same 2-5A binding function as the 80 kDa RNase L and exhibits 2-5A-dependent activity similar to that of the 80 kDa RNase L.

The low molecular weight RNase L has a molecular weight of about 30 kDa under native conditions. Essentially, native conditions are conditions which do not denature proteins, most particularly, conditions which do not denature enzymes. Under the denaturing conditions of SDS-PAGE, low molecular weight RNase L has an apparent molecular weight of about 37 kDa. The 37 kDa mass under denaturing conditions upon SDS-PAGE analysis is in reasonable agreement with the 30 kDa mass under native conditions, based on literature precedents accounting for differences in molecular mass observed under denaturing and native conditions (Somerville etal., *J. Bactedol.* 117:3837–3842, 1995). As used herein, the expressions "30 kDa RNase L", "37 kDa RNase L" and "low molecular weight RNase L" all mean the same molecule, and are used interchangeably herein. As used herein, the expressions "80 kDa RNase L" and "high molecular weight RNase L" mean the same molecule, and are used interchangeably herein.

While biological samples from both normal and CFS-afflicted individuals may contain both the 30 kDa and 80 kDa forms of RNase L, the ratio of the molecules has diagnostic significance. CFS individuals are characterized by a relatively high level of the 30 kDa form and/or a relatively low level of the 80 kDa form. The opposite pattern is observed in healthy individuals. The invention therefore involves determining the level of the 30 and 80 kDa RNase L forms in cells of a biological sample, and determining the ratio of the two forms. The higher the 30 kDa/80 kDa ratio, the more likely the patient is afflicted with CFS.

As demonstrated herein, CFS-afflicted individuals are characterized by a 30 kDa/80 kDa ratio greater than 0.15, typically greater than 0.2. Ratios as high as 0.9 have been observed in CFS patients. Healthy individuals are generally characterized by ratios of less than 0.15, more typically less than about 0.10. In some normal individuals tested the ratio is as low as zero since no 30 kDa RNase L was detected.

According to the present invention, samples are taken from individuals who fit the CDC criteria for CFS suspected of CFS affliction and assayed for the level of the low and high molecular weight RNase L forms. By "level" with respect to the presence of the low and high molecular weight RNase L's in a sample is meant not only a determination of their quantities in the sample in absolute terms, but also embraces determination of a relative presence level as determined by comparison of their amounts to one another, or to a standard value. The sample may be taken from any suitable RNase L-containing cells. Blood or a fraction thereof, such as serum or plasma, may also be employed. RNase L is present in substantial concentrations in mononuclear cells. Thus, a preferred cellular source for samples comprises peripheral blood mononuclear cells (PBMC). The sample may be prepared by collecting cells by centrifugation, disrupting the cells, and removing the cell debris to obtain a cell-free extract. The extract is then examined for the level of the 30 kDa and 80 kDa RNase L RNase L forms.

According to one embodiment of the invention, PBMC are separated from heparinized blood by Ficoll-Hypaque density gradient centrifugation, and cytoplasmic extracts are prepared, according to the procedures of Suhadolnik et al., *Biochemistry* 22:4153–4158 (1983). To avoid loss of RNase L activity, preparation of the cytoplasmic extracts should be commenced within about two hours of blood collection. Briefly, heparinized whole blood is diluted 1:1 with PBS. Two volumes of diluted blood are overlayered on 1 volume of Ficoll-Hypaque (Boyum, *Scand. J. Clin. Lab. Invest.* 97:1–109, 1968) at a density of 1.077 and centrifuged at 20° C., for 30 minutes at 5000×g. The PBMC layer is removed and washed once with 5 volumes of PBS. Isolated PBMC are resuspended in 5 mL of red blood cell lysing buffer (155 mM $NH_4Cl$, 10 mM $NaHCO_3$, pH 7.4, 0.1 mM EDTA), kept on ice for 5 minutes, and washed twice with PBS. The isolated PBMC are resuspended in 0.1 or 0.2 ml (approximately 10 times cell volume) of a buffer (20 mM HEPES, pH 7.5, 5 mM $MgCl_2$, 120 mM KCl, 10% glycerol, 1 mM dithiothreitol) containing 0.5% NONIDET P-40 and kept on ice 10 minutes to lyse the cells. Cytoplasmic extracts are obtained by centrifugation for 6 minutes at 8000×g and 25 ° C. Cell-free extracts may be stored indefinitely at −70° C.in either 25- or 50- $\mu$L aliquots.

A protease inhibitor may be optionally added to the cell extract to stabilize the extract and impede the action of proteases. For example, Mini-Complete™ protease inhibitor cocktail tablets (Boehringer/Mannheim) may be utilized according to the manufacturer's directions. Mini-Complete™ inhibitor contains aprotinin, leupeptin, pefabloc® SC and EDTA. The expression "added protease inhibitor" as used herein in connection with the preparation of cell extracts for diagnostic testing means exogenously added protease inhibitor, beyond the protease inhibitor which may naturally occur in the cell extract. When an extract is said to "be prepared in the presence of added protease inhibitor," what is meant is an amount of protease inhibitor which is sufficient to substantially completely inhibit the activity of proteases present in the extract.

According to one embodiment of the invention, the proteins of the cell-free extract are fractionated according to molecular weight under native, nondenaturing conditions. The relative amounts of the 30 and 80 kDa RNase L molecules in the separated fractions may be assessed by comparing the respective enzyme activities. The 30 and 80 kDa fractions are assayed for 2-5A-dependent RNase L activity in the presence of 2-5A or analog thereof capable of binding to and activating RNase L. By "native conditions" is meant fractionation by a process which substantially preserves the activity of RNase L species in the sample. Essentially, native conditions are conditions which do not denature proteins, most particularly, conditions which do not denature enzymes. Nondenaturing conditions for fractionating proteins according to molecular weight are well-known to those skilled in the art. Nondenaturing fractionation of proteins according to molecular weight is most advantageously carried out by gel filtration high performance liquid chromatography. One column chromatography material for this purpose is SUPERDEX 200 from Pharmacia LKB Biotechnology, Piscataway, N.J. This material is effective in fractionating proteins having molecular weights in the range of 15 kDa to 200 kDa.

2-5A-Dependent RNase L activity may be determined by a number of different RNase L assays. The RNase L activity assay may take the form of a core-cellulose assay (Silverman et al.,*Anal. Biochem.* 144:450–460, 1985, incorporated herein by reference), which involves immobilizing and partial purifying of 2-5A binding molecules on 2-5A core-cellulose, and measuring RNase L activity in the sample by conversion of poly(U)[$^{32}$P]pCp to acid-soluble fragments.

Alternatively, 2-5A-dependent RNase L activity may be detected by a ribosomal RNA cleavage assay, and detection of highly characteristic specific cleavage products (SCPs) (Suhadolnik et al., *Clin. Infect. Dis.*, supra, incorporated herein by reference). Accordingly, the molecular weight fractions are incubated with cytoplasmic extracts (140 $\mu$g of protein per assay) of an RNase L-deficient subclone of L929 cells (the source of intact 28S and 18S ribosomal RNA) at 30° C. for 60 minutes. Total RNA is extracted, denatured and analyzed by electrophoresis on 1.8% agarose gels. After ethidium bromide staining, RNA bands are visualized under ultraviolet light. The formation of SCPs due to RNase L activity may be quantitated by densitometric tracings of gel photographs and expressed as the ratio of the products of the reaction (SCPs) to the substrate (28S and 18S rRNA) remaining at the end of the incubation period. For a discussion of SCPs see Wreschner et al., *Nature* 289:414–417 (1981), the entire disclosure of which is incorporated herein by reference.

According to yet another method, 2-5A-dependent RNase L activity may be determined by assaying the hydrolysis of a suitably labeled RNase L substrate, such as a radiolabeled substrate. For example, RNase L activity in a protein fraction may be determined by contacting the fraction with the substrate poly(U)-3'-[$^{32}$P]pCp in the presence of $p_3A_3$, followed by a radioactivity assay by scintillation spectrometry.

Accordingly, extracts of PBMC (200 $\mu$g protein) are fractionated under native conditions on a Superdex 200 gel filtration column. RNase L activity in fractions is determined by the hydrolysis of poly(U)-3'-[$^{32}$P]pCp (20,000 dpm) in reaction mixtures (15–30 $\mu$l) containing $p_3A_3$ ($1\times10^{-8}$ M to $1\times10^{-7}$ M) (Sobol et al., *J. Biol. Chem.* 270:5963–5978, 1995). The determination of non-specific RNase activity is measured by hydrolysis of poly(C)-3'-[$^{32}$P]pCp (14,000 dpm) in reaction mixtures (15–30 $\mu$l) in the absence of $p_3A_3$. Radioactive measurements are accomplished using Scintiverse I (Fisher) (>99% efficiency).

As an alternative to fractionation according to molecular weight, the proteins of the patient sample may be partially purified by conventional methods using salts such as ammonium sulfate and solvents such as acetone or butyl alcohol, followed by diethylaminoethyl-cellulose chromatography. This methodology results in protein separation on the basis of charge. The 30 and 80 kDa forms of RNase L may be separated by this method based upon total charge differences.

According to anotherembodiment of the invention, the 30 and 80 kDa RNase L forms are quantitated in cell extracts by photoaffinity labeling with a photoprobe comprising a 2-5A azido analog, followed by immunoprecipitation with RNase L antibody and molecular weight fractionation. Under the denaturing conditions of this separation method, the low molecular weight RNase L is detected as a protein having an apparent weight of about 37 kDa upon SDS-PAGE. This methodology specifically identifies 2-5A binding, RNase L immunoreactive proteins, and eliminates proteins which immunoreact with the RNase L antibody, but which are not 2-5A binding proteins. The methodology also eliminates 2-5A binding proteins which are not immunoreactive with the antibody.

The photoprobe used in the photolabeling/immunoprecipitation/fractionation assay comprises an analog of 2-5A according to formula 1, above, wherein either or both of the 2- or 8-hydrogens of one or more of the 2-5A molecule's adenine residues are replaced by an azido group. Photolabeling of 2-5A binding proteins in cell extracts comprises contacting the extract with labeled photoprobe (e.g., radiolabeled) under conditions sufficient to form covalent conjugates of the photoprobe and 2-5A binding proteins. Generally, this is accomplished by incubation of a mixture of the extract and the photoprobe under low intensity ultraviolet light. The preparation of the 2-5A azido analogs for use as photoprobes is described in U.S. Pat. No. 4,990,498 (enzymatic synthesis) and Charubala et al., *Helv. Chim. Acta* 72:1354–1361 (1989) (chemical synthesis). The entire disclosures of both documents are incorporated herein by reference. The 2-5A azido analogs effectively bind to and activate RNase L. By virtue of the photosensitive azido group, the 2-5A azido analogs readily form reactive nitrene radical intermediates (C—N) upon exposure to low intensity ultraviolet light. The nitrene radical intermediate reacts with, and covalently photolabels, biological molecules. The in situ photoactivation of the 2-5A azido analogs following binding to RNase L does not interfere with RNase L activity (See U.S. Pat. No. 4,990,498, FIG. 2).

The 2-5A azido analog according to formula I may comprise an oligomer of a single azido-AMP species (e.g., 2-azido-AMP), as in the case of 2-azidoadenylyl-(2'→5')2-azidoadenylyl-(2'→5')2-azidoadenosine; an oligomer of both 2-azido-AMP and 8-azido-AMP, as in the case of 2-azidoadenylyl-(2'→5')8-azidoadenylyl-(2'→5')2-azidoadenosine; an oligomer of AMP and 2-azido-AMP or 8-azido-AMP, as in the case of 2-azidoadenylyl-(2'→5')2-azidoadenylyl-(2'→5')2-azidoadenosine; or an oligomer resulting from any combination of any of the monomers AMP, 2-azido-AMP, 8-azido-AMP, or 2,8-diazido-AMP, provided at least one of such monomer is an azido-AMP species.

The 2-5A azido analog of formula 1, for use in the practice of the present invention, is preferably a trimer (n=1). The preferred degree of 5'-phosphorylation is monophosphorylation (m=1). Particularly preferred are oligomers containing one or more 8-azidoadenylyl residues, particularly 2-5A azido analogs wherein the 2'-terminal nucleotide is 8-azidoadenosine, e.g., 5'-O-phosphoryl-adenylyl-(2'→5')-adenylyl-(2'→5')-8-azidoadenosine.

The 2-5A azido analog preferably bears a detectable label, permitting its identification. The label may comprise, for example, a radiolabel, such as $^{32}$P, $^{3}$H, $^{14}$C or $^{15}$N. 32p is the strongest β-particle emitter and is therefore preferred. Alternatively, the label may comprise one or more incorporated etheno groups, which strongly fluoresce. The amino group on carbon-6 of one or more of the adenine nuclei may be converted to etheno groups to form $N^1N^6$-ethenoadenine, or the fluorescent oligomer may be synthesized de novo from etheno-AMP, or from a combination of etheno-AMP, azido AMP monomer and AMP monomers, provided at least one monomer comprises etheno-AMP. See Suhadolnik et al., *J. Biol. Chem.* 252:4125–4133 (1977), the entire disclosure of which is incorporated herein by reference. Other labels for detecting biological molecules are known to those skilled in the art.

Following photolabeling with the 2-5A azido analogue, the cell extract is then combined with RNase L polyclonal antibody. The antibody for the immunoprecipitation step may comprise polyclonal antisera raised against human recombinant 80 kDa, which antisera also recognizes the low molecular weight RNase L. Recombinant human 80 kDa RNase L may be expressed by standard recombinant techniques from the known full-length cDNA (Zhou et al., *Cell* 72:753–765, 1993, incorporated herein by reference; GenBank sequence, accession number L10381, incorporated herein by reference). Polyclonal antisera against the recombinant human 80 kDa RNase L is obtained by immunizing animals with the recombinant protein and harvesting the antisera, through known techniques.

The RNase L antibody may comprise an intact antibody, or fragments thereof capable of binding antigen, including but not necessarily limited to, Fab and F (ab')$_2$ fragments. Hence, as used herein, the term "antibody" includes intact antibody molecules and fragments thereof which retain antigen binding ability. A labeled secondary antibody may be optionally employed to aid in the identification of antigen-antibody complexes formed by the RNase L antibody. The secondary antibody is capable of binding to RNase L, or to the primary RNase L antibody. The labeled secondary antibody may comprise, for example, sheep-, goat-, or mouse anti-rabbit IgG, in the case where the primary RNase L antibody is a rabbit antibody.

The label on the secondary antibody is detected by physical or chemical means. Such labels include radiolabels; chromophoric labels such as fluorescent, ultraviolet-absorbing or light absorbing labels; and enzyme labels. Any appropriate radioisotope may be used as the label, for example $^{125}$I, $^{131}$I, $^{3}$H, and $^{14}$C. In an ELISA, the label is an enzyme, e.g. alkaline phosphatase, which cleaves a chromogenic substrate to release a chromophoric cleavage product. In the case of alkaline phosphatase, the substrate may comprise, for example, phenolphthalein monophosphate or p-nitrophenylphosphate.

Following immunoprecipitation, the complexes comprising antibody, photoprobe and 2-5A binding protein formed in the extract are then purified by absorption by Protein A-resin (e.g., Protein-A agarose), followed by washing and elution of proteins from the resin. The eluted protein mixture is fractionated by gel electrophoresis and the photolabeled/immunoprecipitated 2-5A binding proteins are visualized by detection of the label carried on the photoprobe or antibody. The molecular weights of the labeled bands are determined by reference to known molecular weight standards.

It may be appreciated that the strength of the signal from the detectable label is directly proportional to the amount of the labeled species present in the sample. Thus, according to the invention, the ratio of the low molecular weight (37 kDa under the conditions of the assay) to 80 kDa RNase L in the sample may be conveniently provided in terms of the ratio of signals from the detectable labels in the 37 kDa and 80 kDa bands upon gel electrophoresis.

According to one preferred embodiment of the invention, the detectable label is a radioactive isotope in the 2-5A azido analog, preferably $^{32}$P. The photolabeled and immunoprecipitated 2-5A binding proteins are then visualized by autoradiography and quantification of the radioactive emissions from the dried gel by phosphorimager analysis. Phosphorimager analysis may be carried out using an appropriate commercially available device, such as the Fuji BAS 2000 PHOSPHORIMAGER.

The method of the present invention may be employed in situations where the patient manifests one or more symptoms of CFS, particularly fatigue of excessive duration. The method may be most effectively utilized as an adjunct to a physician diagnosis based upon the CDC guidelines for CFS diagnosis. In one aspect, the method of the invention may be utilized as a rapid screen of profoundly fatigued individuals to identify those individuals who are likely afflicted with CFS and require further evaluation under the CDC guidelines.

The reagents described herein may be pre-packaged in kit form.

The practice of the invention is illustrated by the following non-limiting examples.

EXAMPLE

Quantification of Low and High Molecular Weight RNase L in CFS and Normal Cell Extracts A. Study Subjects and Controls.

Study subjects were 54 individuals who had previously been diagnosed as fulfilling the diagnostic criteria for CFS per the Centers for Disease Control and Prevention (CDC) guidelines of 1994 (Fukuda et al., *Ann. Intem. Med.* 121:953–959, 1994) and healthy controls. Patients and controls were selected from medical practices in Nevada and North Carolina. Criteria for selection of patients and controls and clinical variables at initiation of the study were as described by Suhadolnik et al., *Clin. Infect. Dis.* 18:S96–S104 (1994). At the time of blood sampling, selected symptoms were evaluated on a self-graded symptom checklist. Fourteen control subjects were recruited. Each CFS patient and healthy control underwent a medical history and physical examination. Peripheral blood mononuclear cells (PBMC) were separated from heparinized blood (50 ml) by Ficoll-Hypaque density gradient centrifugation. Preparation of cytoplasmic extracts in the presence of protease inhibitor was according to the manufacturer's directions (Mini-Complete™ protease inhibitor cocktail tablets, Boehringer/Mannheim, containing aprotinin, leupeptin, pefabloc®SC and EDTA), Suhadolnik et al., *Clin. Infect. Dis.*, supra.

B. Production of Recombinant, Human RNase L Polyclonal Antibody.

Full-length human RNase L cDNA is described by Zhou et al., *Cell* 72:753–765 (1993), the entire disclosure of which is incorporated herein by reference, and contained as GenBank accession number L10381, also incorporated herein by reference. The glutathione S-transferase (GST) fusion protein strategy was used to obtain purified recombinant, human 80 kDa RNase L required for production of the RNase L polyclonal antibody. GST-RNase L fusion protein was obtained by expression in *E. coli* according to the procedure described by Sobol et al., *J.Biol. Chem.* 270:5963–5978 (1995), the entire disclosure of which is incorporated herein by reference. A polyclonal antibody against recombinant, human 80 kDa RNase L was elicited in New Zealand white rabbits by immunization with the highly purified recombinant, human GST-RNase L fusion protein. Serum was prepared before immunization and retained as a control (pre-immune serum). Initial inoculation was performed on day 1 with 100 µg of GST-RNase L mixed with an equal volume of complete Freund's adjuvant. Boosts with 50 µg of GST-RNase L (50% native and 50% heat denatured protein) mixed with incomplete Freund's adjuvant were given at 14, 21, 49 and 84 days. Blood samples for antibody production were drawn at 120, 150, and 180 days, preceded by additional boosts. Following hydrolysis of GST-RNase L fusion protein with human thrombin, RNase L was covalently coupled to the glutaraldehyde activated cartridge (Whatman) according to the manufacturers specifications. Sodium borohydride was circulated through the column to reduce the glutaraldehyde that was not coupled to RNase L. The rabbit antiserum containing polyclonal antibody to RNase L was circulated through the glutaraldehyde column for 1 hour at room temperature and eluted according to the manufacturer's specifications. The RNase L polyclonal antibody was characterized by Western blotting using extracts of human 293 cells (ATCC CRL 1573) and an *E. coli* expressed recombinant GST-RNase L fusion protein, as described by Sobol et al., supra.

C. Azido Photoaffinity Labeling and Immunopreciritation of 2-5A Binding Proteins in PBMC Extracts.

Chemical synthesis of the 2-5A azido photoprobe, ApAp (8-azidoA), 5'-monophosphorylation with [$\gamma$-$^{32}$P]ATP and polynucleotide kinase to produce [$^{32}$P]pApAp(8-azidoA) and photolabeling of 2-5A binding proteins in PBMC extracts were as described by Charubala et al., *Helv. Chim. Acta* 72:1354–1361 (1989), the entire disclosure of which is incorporated herein by reference. Photolabeling of the 2-5A binding proteins was thus accomplished by incubation of PBMC extracts (100 µg protein), prepared in the absence of added protease inhibitors, with the 2-5A photoprobe [$^{32}$P]pApAp(8-azidoA) (60 µCi/nmole, 5 µCi) (30 min, 4° C.), followed by UV irradiation (8000 watts/cm$^2$, 30 seconds, 0° C.). The photolabeling mixture was combined with affinity-purified RNase L polyclonal antibody (24 µg protein), Protein A-Sepharose (30 µl) and 100 µl phosphate-buffered saline (PBS), and the mixture was rotated for 1 hr at 4° C. After three PBS washes, the resin was mixed with 40 µl of protein solubilization solution, boiled for 5 minutes and centrifuged (10,600×g, 5 min., room temperature). The supernatant was fractionated by 10% SDS-PAGE. The azido-photolabeled/immunoprecipitated 2-5A binding proteins were visualized by autoradiography of the dried gel. The radioactive emissions from the 37 and 80 kDa bands were quantified by phosphorimager analysis with a Fuji BAS 2000 PHOSPHORIMAGER.

D. Results

The ratio of low (37 kDa) to high (80 kDa) molecular weight RNase L was computed from the phosphorimager data. The data (ratio×10) are set forth in Table 1, below. Utilizing a value of the 37 kDa/80 kDa RNase L greater than 0.15 as being diagnostic for CFS, the molecular diagnosis agreed with the physician diagnosis in 81.5% (44/54) of the physician-diagnosed CFS patients, and in 77% (10/13) of the healthy control patients.

TABLE 1

| Patient # | Physician Diagnosis | 37 kDa/ 80 kDa RNase L × 10 |
| --- | --- | --- |
| 1 | CFS | 66.4 |
| 2 | CFS | 9.9 |
| 3 | CFS | 9.8 |
| 4 | CFS | 9.4 |
| 5 | CFS | 9.2 |
| 6 | CFS | 9.0 |
| 7 | CFS | 8.9 |
| 8 | CFS | 8.8 |
| 9 | CFS | 8.7 |
| 10 | CFS | 8.7 |
| 11 | CFS | 8.3 |
| 12 | CFS | 7.9 |
| 13 | CFS | 7.9 |
| 14 | CFS | 7.6 |
| 15 | CFS | 7.5 |
| 16 | CFS | 7.2 |
| 17 | CFS | 6.5 |
| 18 | CFS | 5.3 |
| 19 | CFS | 5.2 |
| 20 | CFS | 4.8 |
| 21 | CFS | 4.7 |
| 22 | CFS | 4.6 |
| 23 | CFS | 4.6 |
| 24 | CFS | 4.5 |
| 25 | CFS | 4.5 |
| 26 | CFS | 4.4 |
| 27 | CFS | 4.3 |
| 28 | CFS | 4.3 |
| 29 | CFS | 3.8 |
| 30 | CFS | 3.4 |

TABLE 1-continued

| Patient # | Physician Diagnosis | 37 kDa/ 80 kDa RNase L × 10 |
|---|---|---|
| 31 | CFS | 3.2 |
| 32 | CFS | 3.2 |
| 33 | CFS | 3.1 |
| 34 | CFS | 3.1 |
| 35 | CFS | 2.9 |
| 36 | CFS | 2.8 |
| 37 | CFS | 2.7 |
| 38 | CFS | 2.6 |
| 39 | CFS | 2.1 |
| 40 | CFS | 2.1 |
| 41 | CFS | 1.9 |
| 42 | CFS | 1.8 |
| 43 | CFS | 1.7 |
| 44 | CFS | 1.5 |
| 45 | CFS | 1.2 |
| 46 | CFS | 1 |
| 47 | CFS | 0.6 |
| 48 | CFS | 0.6 |
| 49 | CFS | 0.5 |
| 50 | CFS | 0.1 |
| 51 | CFS | 0.03 |
| 52 | CFS | 0 |
| 53 | CFS | 0 |
| 54 | CFS | 0 |
| 55 | Control | 0 |
| 56 | Control | 0 |
| 57 | Control | 0 |
| 58 | Control | 0.2 |
| 59 | Control | 0.2 |
| 60 | Control | 0.3 |
| 61 | Control | 0.3 |
| 62 | Control | 0.5 |
| 63 | Control | 0.5 |
| 64 | Control | 0.6 |
| 65 | Control | 1.9 |
| 66 | Control | 3.5 |
| 67 | Control | 8.9 |

All references cited herein are incorporated by reference.

The present invention may be embodied in other specific forms without departing from the spirit or essential attributes thereof and, accordingly, reference should be made to the appended claims, rather than to the foregoing specification, as indication the scope of the invention.

What is claimed is:

1. A method for diagnosing chronic fatigue syndrome comprising
   determining the level of low molecular weight RNase L and the level of high molecular weight RNase L in a biological sample from a human subject; and
   computing a ratio for the level of low molecular weight RNase L to the level of high molecular weight RNase L in the sample, which ratio is diagnostic for chronic fatigue syndrome.

2. A method according to claim 1 wherein a ratio of low molecular weight to high molecular weight RNase L of greater than 0.15 indicates that the individual is afflicted with chronic fatigue syndrome.

3. A method according to claim 1 wherein the sample comprises blood or a fraction thereof.

4. A method according to claim 1 wherein the level of the low molecular weight RNase L and the level of the high molecular weight RNase L are determined by
   (a) contacting the sample with a probe comprising a compound according to formula I bearing a detectable label, under conditions sufficient to form covalent conjugates of said labeled probe compound and 2',5'-oligoadenylate-binding proteins in the sample:

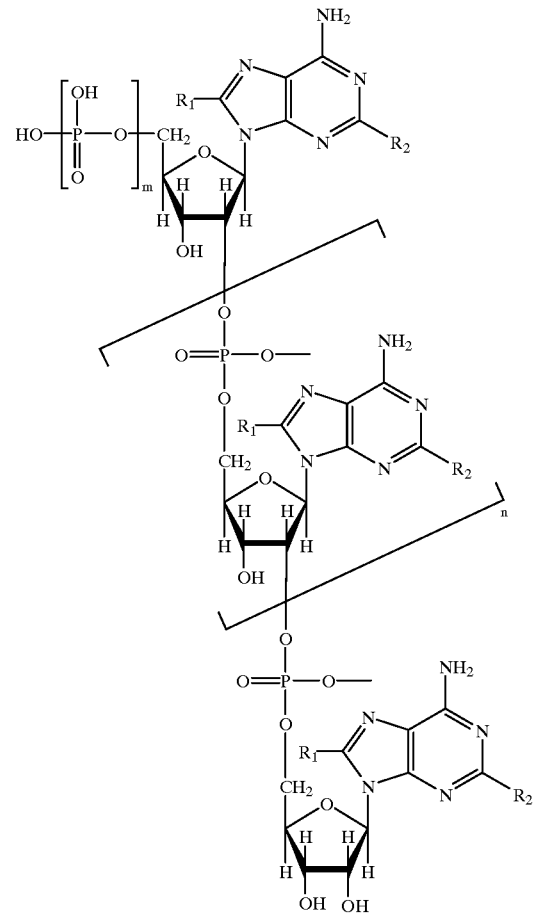

wherein
   m is an integer from 0 to 3,
   n is an integer from 1 to 3, and
   each $R_1$ and each $R_2$ is, independently of each other $R_1$ and $R_2$, hydrogen or $N_3$, provided at least one $R_1$ or $R_2$ is $N_3$, or a water soluble salt of said compound;
   (b) contacting the sample containing said covalent conjugates with an antibody which binds RNase L species in the sample;
   (c) separating the proteins in said sample by gel electrophoresis; and
   (d) quantitating the proteins of about 37 which have apparent molecular weights according to sodium dodecyl sulfate-polyacrylamide gel electrophoresis about 37 kDa and about 80 kDa, which about 37 kDa and about 80 kDa proteins have formed covalent conjugates with the labeled probe compound and which are bound by said antibody.

5. A method according to claim 3 wherein the sample comprises a cytoplasmic extract of peripheral blood mononuclear cells.

6. A method according to claim 4 wherein the sample is prepared in the presence of added protease inhibitor.

7. A method according to claim 4 wherein the conditions for forming said covalent conjugates include ultraviolet irradiation of said sample to covalently bond said probe compound to the 2',5'-oligoadenylate-binding proteins in the sample.

8. A method according to claim 4 wherein n is 1 in the probe compound.

9. A method according to claim 6 wherein the sample comprises blood or a fraction thereof.

10. A method according to claim 8 wherein m is 1 in the probe compound.

11. A method according to claim 9 wherein the sample comprises a cytoplasmic extract of peripheral blood mononuclear cells.

12. A method according to claim 10 wherein each $R_2$ in the probe compound is hydrogen.

13. A method according to claim 11 wherein the detectable label on said probe compound is a radiolabel.

14. A method according to claim 12 wherein the probe compound is 5'-O-phosphoryl-adenylyl-(2'→5')-adenylyl-(2'→5')-8-azidoadenosine, or salt thereof.

15. A method according to claim 13 wherein the radiolabel is a $^{32}P$ atom.

\* \* \* \* \*